United States Patent
Wöldike et al.

(10) Patent No.: US 6,171,823 B1
(45) Date of Patent: Jan. 9, 2001

(54) PROCESS FOR PRODUCING EXTRACELLULAR PROTEINS IN BACTERIA

(75) Inventors: Helle Fabricius Wöldike, Lynge; Sven Hastrup, Copenhagen, both of (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 08/849,602

(22) PCT Filed: Dec. 8, 1995

(86) PCT No.: PCT/DK95/00498

§ 371 Date: Jun. 2, 1997

§ 102(e) Date: Jun. 2, 1997

(87) PCT Pub. No.: WO96/17943

PCT Pub. Date: Jun. 13, 1996

(30) Foreign Application Priority Data

Dec. 9, 1994 (DK) .................................................. 1411/94

(51) Int. Cl.[7] ............................. C12N 15/09; C12N 9/52; C12P 21/06; C07H 21/04
(52) U.S. Cl. .................... 435/69.3; 435/69.1; 435/320.1; 435/220; 435/824; 536/23.2; 935/14
(58) Field of Search .................................. 435/69.3, 69.1, 435/320.1, 220, 824; 536/23.2; 935/14

(56) References Cited

U.S. PATENT DOCUMENTS

| | | | |
|---|---|---|---|
| 5,248,599 | * | 9/1993 | Sakiyama et al. . |
| 5,536,661 | * | 7/1996 | Boel et al. . |
| 5,691,162 | * | 11/1997 | Shuster et al. . |
| 5,693,250 | * | 12/1997 | Branner et al. . |
| 5,702,934 | * | 12/1997 | Hastrup et al. . |

FOREIGN PATENT DOCUMENTS

| | | |
|---|---|---|
| 0 387 646 | 9/1990 | (EP) . |
| 9617943 | * 6/1996 | (WO) . |
| 9733984 | * 9/1997 | (WO) . |

OTHER PUBLICATIONS

Au et al., J. Bacteriol., 173(15) : 4551–4557.
Silen et al., J. Bacteriol., 171(3): 1320–1325.
Tsunasawa et al., J. Biol. Chem. 264(7): 3832–3839.
Ohara et al., J. Biol. Chem. 264(34): 20625–20631.
Silen et al., Gene 69: 237–244.

* cited by examiner

Primary Examiner—Nita Minnifield
(74) Attorney, Agent, or Firm—Steve T. Zelson, Esq.; Reza Green, Esq.

(57) ABSTRACT

The invention relates to a method of producing an extracellular protein in a bacterium provided with an inner and an outer cell membrane, the method comprising: (a) providing a recombinant vector including a DNA construct comprising a DNA sequence encoding the prepropeptide or part of the prepropeptide of a bacterial extracellular protease selected from the group consisting of *Achromobacter lyticus* protease I, Bacillus metalloproteases and Bacillus serine proteases preceding and operably connected to a DNA sequence encoding a desired protein, (b) transforming cells of a microorganism provided with an inner and outer cell membrane with the recombinant vector of step (a), (c) culturing the transformed cells of step (b) under conditions permitting expression of said DNA insert and leakage of the bacterial extracellular protease propeptide fused to the desired protein into the culture medium, and (d) recovering the resulting protein from the medium.

22 Claims, 14 Drawing Sheets

Linker: pSX167: KFN 575/576

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (xi) SEQUENCE DESCRIPTION: SEQ ID NO:1:

CGATCGCATC GGCTGCTGAG GTCTCGCAA                  29

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (xi) SEQUENCE DESCRIPTION: SEQ ID NO:2:

GATCTTGCGA GACCTCAGCA GCCGATGCGA T                                              31

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:3:

ACTCGGCGCG CCAACTGTGG ACGG                                                      24

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:4:

GACCTCTTTA TCATCGTCGT CCTTCTCGCC GGACGCAGCG GCCAGGC                             47

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:5:

GACGACGATG ATAAAGAGGT CTCGCAAGAT CTGTTTAACC                                     40

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

CCAGATTTGA TCCAGTACTC TGGGC                                                     25

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:7:

AAAAAAGCTT GGAGAAACCG AATGAAGAAA C                                              31

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:8:

```
GACCTCTTTA TCATCGTCGT CCATTGTCGT TACTTCTGCA TCCTC           45
```

(2) INFORMATION FOR SEQ ID NO:9:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:9:

```
CGATGAAACG TATCTGCGGA TCCCTGCTGC TGCTGGGTCT GAGCATCAGC GCGGCGCTGG    60

CGGCGCCGG                                                           69
```

(2) INFORMATION FOR SEQ ID NO:10:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:10:

```
CTAGCCGGCG CCGCCAGCGC CGCGCTGATG CTCAGACCCA GCAGCAGCAG GGATCCGCAG    60

ATACGTTTCA T                                                        71
```

(2) INFORMATION FOR SEQ ID NO:11:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:11:

```
CTAGCCGTCC GGCGGCGTTC GATTATGCGA ACCTGAGCAG CGTGGATAAA GTGGCGCTGC    60

GTACCATGCC GGCGG                                                    75
```

(2) INFORMATION FOR SEQ ID NO:12:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:12:

```
TCGACCGCCG GCATGGTACG CAGCGCCACT TTATCCACGC TGCTCAGGTT CGCATAATCG    60

AACGCCGCCG GACGG                                                    75
```

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

```
CAGCAACAAC AACTCGGCGC GCC                                           23
```

(2) INFORMATION FOR SEQ ID NO:14:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (xi) SEQUENCE DESCRIPTION: SEQ ID NO:14:

CGACACGCCC TTCTCTCCGG ACG                                    23

(2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:15:

CCGGAGAACG TG                                                12

(2) INFORMATION FOR SEQ ID NO:16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:16:

GATCCACGTT CT                                                12

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:17:

AGCTTTAATG CGGTAGTTTA TCACAGTTAA ATTG                        34

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

AACTGTGATA AACTACCGCA TTAA                                   24

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

CTAACGCTTA AGGAGGTTAA T                                      21

(2) INFORMATION FOR SEQ ID NO:20:

(i) SEQUENCE CHARACTERISTICS:

(A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:20:

CGATTAACCT CCTTAAGCGT TAGCAATTT                                    29

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:21:

GTGTGACCGA ACCGGGTGTG CTGGGTCAGC GTG                               33

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:22:

GATCCACGCT GACCCAGCAC ACCCGGTTCG GTCACACCG                         39

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

GCGCGACCGG CACCAACCGT G                                            21

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:24:

GATCCACGGT TGGTGCCGGT CGCGCTGCA                                    29

(2) INFORMATION FOR SEQ ID NO:25:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:25:

CATTTGACCG TGCAGTGGCA GCCCTCGGGC GGCGTGACCG AGCCGGGTTC GGCGGGTTCG  60

(2) INFORMATION FOR SEQ ID NO:26:

(i) SEQUENCE CHARACTERISTICS:
        (A) LENGTH: 60 base pairs (B) TYPE: nucleic acid
        (C) STRANDEDNESS: single
        (D) TOPOLOGY: linear (xi) SEQUENCE DESCRIPTION: SEQ ID NO:26:

TTCGCCACCG GCGGATCCGC GCGGCGTGCC GCCGCCCGAA TCCAGGCCAT CGATGAACTG        60

(2) INFORMATION FOR SEQ ID NO:27:

(i) SEQUENCE CHARACTERISTICS:
        (A) LENGTH: 653 amino acids
        (B) TYPE: amino acid
        (C) STRANDEDNESS: single
        (D) TOPOLOGY: linear (xi) SEQUENCE DESCRIPTION: SEQ ID NO:27:

```
Met Lys Arg Ile Cys Gly Ser Leu Leu Leu Gly Leu Ser Ile Ser
 1               5                  10                  15

Ala Ala Leu Ala Ala Pro Ala Ser Arg Pro Ala Ala Phe Asp Tyr Ala
                20                  25                  30

Asn Leu Ser Ser Val Asp Lys Val Ala Leu Arg Thr Met Pro Ala Val
                35                  40                  45

Asp Val Ala Lys Ala Lys Ala Glu Asp Leu Gln Arg Asp Lys Arg Gly
 50                  55                  60

Asp Ile Pro Arg Phe Ala Leu Ala Ile Asp Val Asp Met Thr Pro Gln
 65                  70                  75                  80

Asn Ser Gly Ala Trp Glu Tyr Thr Ala Asp Gly Gln Phe Ala Val Trp
                85                  90                  95

Arg Gln Arg Val Arg Ser Glu Lys Ala Leu Ser Leu Asn Phe Gly Phe
                100                 105                 110

Thr Asp Tyr Tyr Met Pro Ala Gly Gly Arg Leu Leu Val Tyr Pro Ala
                115                 120                 125

Thr Gln Ala Pro Ala Gly Asp Arg Gly Leu Ile Ser Gln Tyr Asp Ala
                130                 135                 140

Ser Asn Asn Asn Ser Ala Arg Gln Leu Trp Thr Ala Val Val Pro Gly
145                 150                 155                 160

Ala Glu Ala Val Ile Glu Ala Val Ile Pro Arg Asp Lys Val Gly Glu
                165                 170                 175

Phe Lys Leu Arg Leu Thr Lys Val Asn His Asp Tyr Val Gly Phe Gly
                180                 185                 190

Pro Leu Ala Arg Arg Leu Ala Ala Ala Ser Gly Glu Lys Gly Val Ser
                195                 200                 205

Gly Ser Cys Asn Ile Asp Val Val Cys Pro Glu Gly Asp Gly Arg Arg
                210                 215                 220

Asp Ile Ile Arg Ala Val Gly Ala Tyr Ser Lys Ser Gly Thr Leu Ala
225                 230                 235                 240

Cys Thr Gly Ser Leu Val Asn Asn Thr Ala Asn Asp Arg Lys Met Tyr
                245                 250                 255

Phe Leu Thr Ala His His Cys Gly Met Gly Thr Ala Ser Thr Ala Ala
                260                 265                 270

Ser Ile Val Val Tyr Trp Asn Tyr Gln Asn Ser Thr Cys Arg Ala Pro
                275                 280                 285

Asn Thr Pro Ala Ser Gly Ala Asn Gly Asp Gly Ser Met Ser Gln Thr
                290                 295                 300

Gln Ser Gly Ser Thr Val Lys Ala Thr Tyr Ala Thr Ser Asp Phe Thr
305                 310                 315                 320
```

-continued

```
Leu Leu Glu Leu Asn Asn Ala Ala Asn Pro Ala Phe Asn Leu Phe Trp
            325                 330                 335

Ala Gly Trp Asp Arg Arg Asp Gln Asn Tyr Pro Gly Ala Ile Ala Ile
            340                 345                 350

His His Pro Asn Val Ala Glu Lys Arg Ile Ser Asn Ser Thr Ser Pro
            355                 360                 365

Thr Ser Phe Val Ala Trp Gly Gly Ala Gly Thr Thr His Leu Asn
            370                 375             380

Val Gln Trp Gln Pro Ser Gly Gly Val Thr Glu Pro Gly Ser Ser Gly
385                 390                 395                 400

Ser Pro Ile Tyr Ser Pro Glu Lys Arg Val Leu Gly Gln Leu His Gly
            405                 410                 415

Gly Pro Ser Ser Cys Ser Ala Thr Gly Thr Asn Arg Ser Asp Gln Tyr
            420                 425                 430

Gly Arg Val Phe Thr Ser Trp Thr Gly Gly Ala Ala Ala Ser Arg
            435                 440                 445

Leu Ser Asp Trp Leu Asp Pro Ala Ser Thr Gly Ala Gln Phe Ile Asp
450                 455                 460

Gly Leu Asp Ser Gly Gly Gly Thr Pro Asn Thr Pro Pro Val Ala Asn
465                 470                 475                 480

Phe Thr Ser Thr Thr Ser Gly Leu Thr Ala Thr Phe Thr Asp Ser Ser
            485                 490                 495

Thr Asp Ser Asp Gly Ser Ile Ala Ser Arg Ser Trp Asn Phe Gly Asp
            500                 505                 510

Gly Ser Thr Ser Thr Ala Thr Asn Pro Ser Lys Thr Tyr Ala Ala Ala
            515                 520                 525

Gly Thr Tyr Thr Val Thr Leu Thr Val Thr Asp Asn Gly Gly Ala Thr
            530                 535                 540

Asn Thr Lys Thr Gly Ser Val Thr Val Ser Gly Gly Pro Gly Ala Gln
545                 550                 555                 560

Thr Tyr Thr Asn Asp Thr Asp Val Ala Ile Pro Asp Asn Ala Thr Val
            565                 570                 575

Glu Ser Pro Ile Thr Val Ser Gly Arg Thr Gly Asn Gly Ser Ala Thr
            580                 585                 590

Thr Pro Ile Gln Val Thr Ile Tyr His Thr Tyr Lys Ser Asp Leu Lys
            595                 600                 605

Val Asp Leu Val Ala Pro Asp Gly Thr Val Tyr Asn Leu His Asn Arg
            610                 615                 620

Thr Gly Gly Ser Ala His Asn Ile Ile Gln Thr Phe Thr Lys Asp Leu
625                 630                 635                 640

Ser Ser Glu Ala Ala Gln Arg Ala Pro Gly Ser Cys Gly
            645                 650
```

(2) INFORMATION FOR SEQ ID NO:28:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:28:

AAAAACTGCA GCGCTCGCCG CCCCGGCCTC GC                              32

(2) INFORMATION FOR SEQ ID NO:29:

-continued

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:29:

AAAAAGGTAC CGGTCGCGAC GGTCCCAACC GGCCC                                       35
```

PROCESS FOR PRODUCING EXTRACELLULAR PROTEINS IN BACTERIA

CROSS-REFERENCE TO RELATED APPLICATIONS

Figure 1:
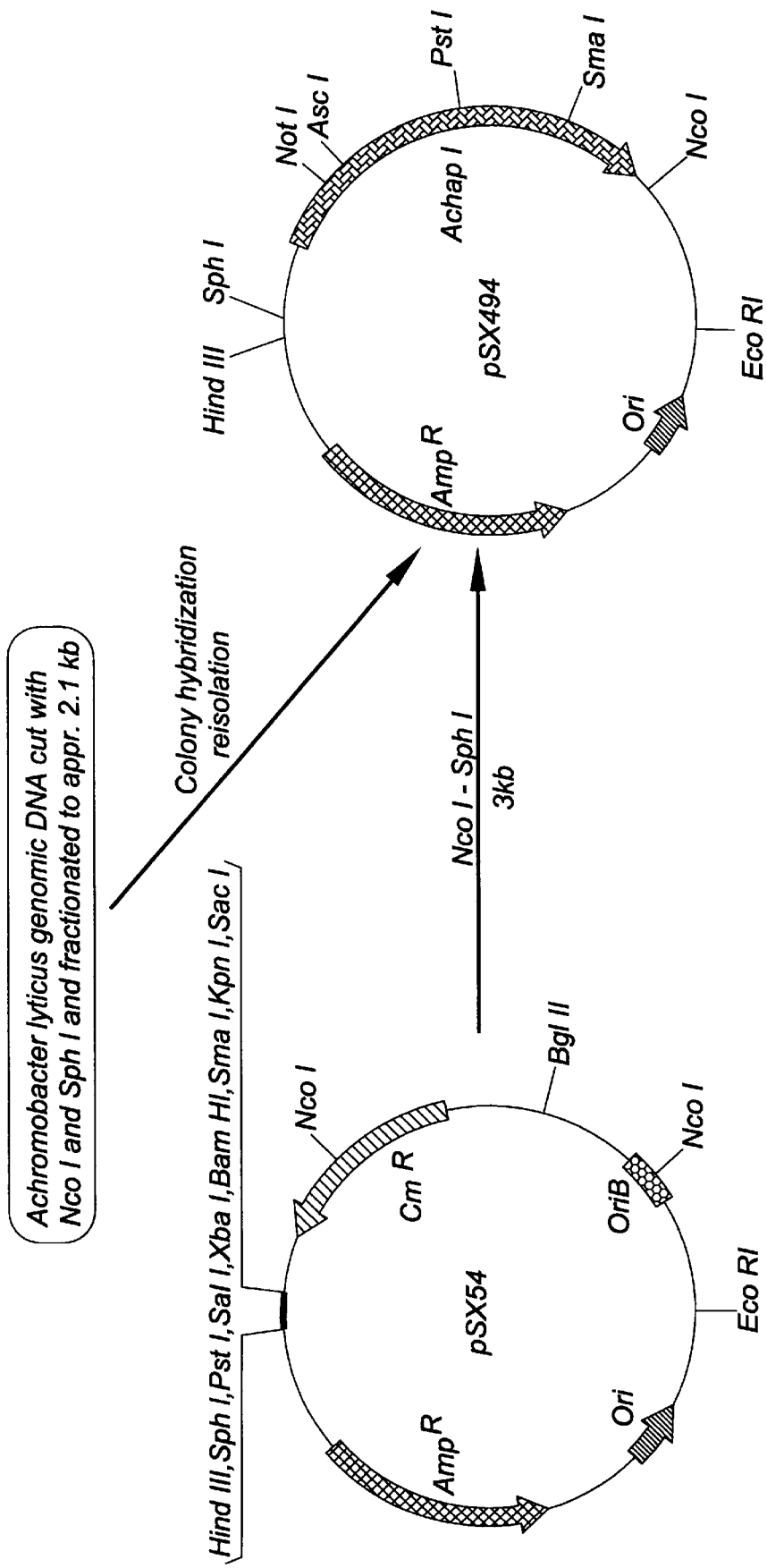

This application is a 35 U.S.C. 371 national application of PCT/DK95/00498 filed Dec. 8, 1995, and claims priority under 35 U.S.C. 119 of Danish application 1411/94 filed Dec. 9, 1994, the contents of which applications are fully incorporated herein by reference.

FIELD OF INVENTION

The present invention relates to a method of producing an extracellular protein in a bacterium, as well as to a DNA construct and a recombinant vector comprising a DNA sequence encoding said protein.

BACKGROUND OF THE INVENTION

Prokaryotic organisms provided with both an inner and outer cell membrane such as gram-negative bacteria only rarely secrete proteins out of the cell into the surrounding medium. Such proteins which do not remain in the cytoplasm are usually exported across the cytoplasmic membrane into the periplasmic space but do not cross the outer cell membrane. However, more recently examples have been found of proteins which are truly secreted from gram-negative bacteria.

Thus, *Lysobacter enzymogenes* secretes an alkaline phosphatase (cf. S. Au et al., *J. Bacteriol.* 173(15), 1991, pp. 4551–4557) and an α-lytic protease. Attempts to express the α-lytic protease in *E. coli* have resulted in production of the enzyme within cells as well as in the extracellular medium (cf. J. L. Silen et al., *J. Bacteriol.* 171(3), 1989, pp. 1320–1325).

Likewise, *Achromobacter lyticus* produces an extracellular protease, the primary structure of which appears from S. Tsunasawa et al., *J. Biol. Chem.* 264(7), 1989, pp. 3832–3839. The gene encoding *A. lyticus* protease I was cloned in *E. coli* in which the enzyme was exported to the periplasm rather than secreted into the culture medium (cf. T. Ohara et al., *J. Biol. Chem.* 264(34), 1989, pp. 20625–20631).

SUMMARY OF THE INVENTION

It has now been found possible to obtain extracellular production of proteins from a heterologous host bacterium which does not readily translocate proteins out of the cells. Such extracellular production is accomplished by means of a prepropeptide or part of a prepropeptide of certain bacterial extracellular proteases.

Accordingly, the present invention relates to a method of producing an extracellular protein in a bacterium provided with an inner and outer cell membrane, the method comprising (a) providing a recombinant vector including a DNA construct comprising a DNA sequence encoding the prepropeptide or part of the prepropeptide of a bacterial extracellular protease selected from the group consisting of *Achromobacter lyticus* protease I, Bacillus metalloproteases and Bacillus serine proteases preceding and operably connected to a DNA sequence encoding a desired protein, (b) transforming cells of a bacterium provided with an inner and outer cell membrane with the recombinant vector of step (a), (c) culturing the transformed cells of step (b) under conditions permitting expression of said DNA insert and leakage of the bacterial extracellular protease propeptide fused to the desired protein into the culture medium, and (d) recovering the resulting protein from the medium.

In the present context, the term "bacterium provided with an inner and outer cell membrane" is intended to indicate a bacterium which has an inner, or cytoplasmic, membrane surrounding the cytoplasm of the cell as well as an outer membrane and a periplasmic space between the inner and outer membrane. In most such organisms, there are mechanisms (including signal sequences) permitting the translocation of expressed gene products across the inner membrane to the periplasm, while secretion of protein s through the outer membrane is far less common. The term "heterologous", when applied to host cells, is intended to indicate that the host cell is one which does not, in nature, produce the protein in question.

The term "prepropeptide" is intended to indicate a peptide composed of a signal peptide (the prepeptide) and one or m ore peptide sequences present on a precursor form of the protein to be produced. If a part (or fragment) of a prepropeptide is employed in the method of the invention, it should be sufficient in length to have retained the ability of the full-length prepropeptide to bring about extracellular production of the protein of interest.

The term "bacterial extracellular protease" is intended to indicate a proteolytic enzyme produced in bacteria and secreted from bacterial cells. Examples of suitable bacterial extracellular proteases are *Achromobacter lyticus* protease I, Bacillus metalloproteases and Bacillus serine proteases, such as subtilisins.

The term "operably connected" is intended to indicate that the DNA sequence encoding the prepropeptide is transcribed together with the DNA sequence encoding the desired protein.

The protein produced by the present method may be either homologous or heterologous, either to the prepropeptide or to the host cell or both. Thus, it may be envisaged that the DNA sequence encoding the protein of interest may be preceded by a DNA sequence encoding a prepropeptide which, in nature, is connected to the protein-coding DNA sequence expressed in a host bacterium which does not naturally produce the protein. Alternatively, the DNA sequence encoding the protein of interest may be preceded by a DNA sequence encoding a prepropeptide which is not naturally connected to the protein-coding DNA sequence expressed in a host bacterium which produces the protein in nature. Furthermore, the DNA sequence encoding the protein of interest may be preceded by a DNA sequence encoding a prepropeptide which is not naturally connected to the protein-coding DNA sequence expressed in a host bacterium which does not naturally produce the protein.

The term "leakage" is intended to indicate that the protein produced by the present method is transported out of the cell either by secretion, i.e. translocation across both the inner and outer cell membrane, or by export of the protein to the periplasm followed by lysis of the outer membrane. The lysis of the outer membrane may be complete or partial, or the protein produced by the present method is transported out of the cell by export of the protein to the periplasm followed by release through the outer cell membrane.

In another aspect, the present invention relates to a method of producing an extracellular protein in a bacterium provided with an inner and outer cell membrane, in which method a bacterium provided with an inner and outer cell membrane and transformed with a recombinant vector including a DNA construct comprising a DNA sequence encoding the prepropeptide or part of the prepropeptide of a bacterial extracellular protease selected from the group consisting of Achromobacter lyticus protease I, Bacillus metalloproteases and Bacillus serine proteases preceding and operably connected to a DNA sequence encoding a desired protein, is cultured under conditions permitting expression of said DNA insert and leakage of the bacterial extracellular protease propeptide fused to the desired protein into the culture medium, and the resulting protein is recovered from the medium.

In a further aspect, the present invention relates to a recombinant expression vector including a DNA construct comprising a DNA sequence encoding the prepropeptide or part of the prepropeptide of a bacterial extracellular protease selected from the group consisting of Achromobacter lyticus protease I, Bacillus metalloproteases and Bacillus serine proteases preceding and operably connected to a DNA sequence encoding a desired protein. The vector is useful for transformation of a suitable host microorganism in the method of the invention described above.

In a still further aspect, the present invention relates to a DNA construct comprising a DNA sequence encoding the prepropeptide or part of the prepropeptide of a bacterial extracellular protease selected from the group consisting of Achromobacter lyticus protease I, Bacillus metalloproteases and Bacillus serine proteases preceding and operably connected to a DNA sequence encoding a desired protein. The DNA construct may suitably be inserted into a recombinant vector as indicated above.

DETAILED DESCRIPTION OF THE INVENTION

Figure 11:
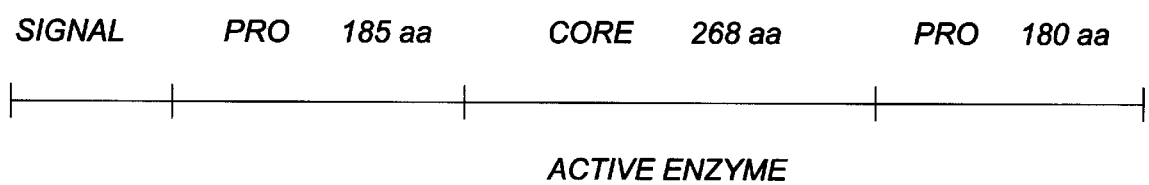

In the
Acromobacter lyticusgenome, the gene coding for *A. lyticus* protease I encodes a polypeptide of 653 amino acid residues SEQ ID NO:27. This includes a signal (or pre) peptide of 20 amino acids, an N-terminal propeptide of 185 amino acids, a core protein of 268 amino acids which is the active protease, and a C-terminal propeptide of 180 amino acids, as shown in FIG. 11 (cf. T. Ohara et al., *J. Biol. Chem.* 264, 1989, pp. 20625–20630).

In a preferred embodiment of the invention, the DNA construct comprises a DNA sequence encoding the prepeptide and a 185 amino acid N-terminal propeptide, but not the 180 amino acid C-terminal propeptide, of *A. lyticus* protease I. It has surprisingly been found possible to omit the C-terminal propeptide while obtaining extracellular production of the desired protein. Omission of the C-terminal propeptide results in the formation of a homogeneous extracellular product which is, for instance, easier to purify than the heterogeneous product obtained when the C-terminal propeptide is present. The DNA construct may further comprise a DNA sequence encoding at least part of the *A. lyticus* protease I, as such a sequence has been found to facilitate transport of the desired protein out of the host cell. If such a DNA sequence is included in the construct, it may encode full-length *A. lyticus* protease I core protein. The protease may either be in active form, or it may be inactivated, e.g. by deletion of one or more amino acids at the C-terminal end of the protease, or by substitution of one or more of the amino acids of the catalytic triad (His57, Asp113 and Ser194). For example, Ser194 may suitably be substituted by Ala.

Examples of desired proteins are *A. lyticus* protease I core protein, glucagon-like peptide-1, growth hormone, tissue factor pathway inhibitor, aprotinin, trypsin, insulin or an insulin precursor or analogue, or enzymes such as lipases, amylases, cellulases or proteases.

The DNA construct of the invention encoding the desired protein may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The DNA construct of the invention encoding the protein may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phosphoamidite method, oligonucleotides are synthesized, e.g. in an automatic DNA synthesizer, purified, annealed, ligated and cloned in suitable vectors.

Furthermore, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The DNA construct may also be prepared by polymerase chain reaction using specific primers, for instance as described in *PCR Protocols*, 1990, Academic Press, San Diego, Calif., USA. For instance, it may be envisaged that the DNA sequence encoding the prepropeptide may be prepared by PCR amplification of chromosomal DNA of the species from which the prepropeptide is derived. Likewise, the DNA sequence encoding the desired protein may be prepared by PCR amplification of chromosomal DNA from the species from which the protein is derived, or for instance by screening a genomic or cDNA library with oligonucleotides as indicated above.

The recombinant vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the desired protein is operably linked to addit ional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the protein.

The promoter may be any DNA sequence which shows transcriptional activity in the host cell of choice and may be derived from genes encoding proteins either homologous or heterologous to the host cell. The promoter is preferably an inducible promoter, and more particularly one where expression from the promoter may be turned off by a repressor under non-induced conditions. Examples of inducible promoters include the phage Lambda $P_R$ or $P_L$ promoters or the *E. coli* lac, trp or tac promoters.

The vector may also comprise a selectable marker, e.g. a gene the product of which confers resistance to a drug, e.g. ampicillin, kanamycin, tetracyclin or chloramphenicol.

The procedures used to ligate the DNA sequences coding for the desired protein, the promoter and preprosequence, respectively, and to insert them into suitable vectors containing the information necessary for replication, are well known to persons skilled in the art (cf., for instance, Sambrook et al., *Molecular Cloning: A Laboratory Manual*, Cold Spring Harbor Laboratory, Cold Spring Harbor, N.Y., USA).

The bacterial host cell into which the DNA construct or the recombinant vector of the invention is introduced may be any cell which is capable of extracellularly producing the desired protein and includes gram-negative bacteria such as *Echerichia coli* or Pseudomonas. The transformation of the bacteria may be effected by protoplast transformation or by using competent cells in a manner known per se (cf. Sambrook et al., supra).

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The protein produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of protein in question.

The protein recovered in step (d) of the method of the invention may be in precursor form, i.e. it is recovered as a polypeptide comprising the propeptide fused to the protein. In this case, the precursor may subsequently be subjected to maturation, in particular by enzymatic processing procedures known per se in the art. The enzyme used for maturation is usually so selected that it is is specific for the amino acid residue(s) at the desired cleavage site. Examples of such enzymes are trypsin, trypsin-like protease derived from *Fusarium oxysporum* (WO 89/6270), clostripain (W. M. Mitchell et al., *Methods Enzymol.* 19, 1970, p. 635), mouse submaxillary gland protease (M. Levy et al., *Methods Enzymol.* 19, 1970, p. 672), thrombin or other proteolytic enzymes of the blood coagulation cascade (e.g. Factor Xa), bovine enterokinase, *Staphylococcus aureus* V8 protease, or *Bacillus licheniformis* Glu/Asp-specific serine protease. If no appropriate cleavage site is present in the precursor polypeptide, it may be provided, e.g. by site-directed mutagenesis of the DNA sequence coding for the precursor to introduce one or more codons specifying the desired amino acid residue(s).

The invention is further illustrated in the following examples which are not in any way intended to limit the scope of the invention as claimed.

EXAMPLE 1

Based on the published sequence of the gene coding for the *Achromobacter lyticus* protease I (Ohara et al. (1989), J. Biol. Chem 264, 20625–20631) PCR primers were synthetizised in order to amplify either the first half, the second half, or the whole gene when using *Achromobacter lyticus* M497-1 chromosomal DNA as template in the PCR reactions.

Chromosomal DNA was prepared from *Achromobacter lyticus* M-497-1 following the procedure of Kamelendu Nath (Nucleic Acids Res. 18(21), 1990, p. 6442) with a start volume of 50 ml over night LB culture.

A fragment of the gene was amplified by using the two primers:

MHJ783:
5'-AAAAACTGCAGCGCTCGCCGCCCCGGCCTC GC-3' SEQ ID NO:28 (introduces a Pst I site in the signal sequence coding part of the gene)

MHJ782:
5'-AAAAAGGTACCGGTCGCGACGGTCCCAACC GGCCC-3' SEQ ID NO:29 (introduces a Kpn I site in the middle part of the region coding for the mature enzyme)

Reaction mixture:
10 µl 10×PCR buffer
8 µl 2.5 mM dNTP
10 µl 10 pmol/µl primer MHJ783
10 µl 10 pmol/µl primer MHJ782
0.5 µg A. *lyticus* M497-1 DNA
59.5 µl H$_2$O
0.5 µl Taq polymerase (added at 95° C.)

The reaction was run for 30 cycles under the following conditions:

| Denaturing | 95° C. | 1 min |
| Annealing | 72° C. | 1 min |
| Polymerization | 72° C. | 2 min |

5 µl of the reaction mixture was run on a 1% agarose gel and a band of the right size (997 bp) was observed.

The DNA could be digested with Asc I, Not I, Sal I, and Xho I as was expected for the protease gene.

50 µl of the reaction mixture was digested with Pst I and Kpn I, isolated from an agarose gel and ligated into pUC19 (C. Yanisch-Perron et al., Gene 33, 1985, pp. 103–119) digested with the same enzymes. The ligation mixture was transformed into *E. coli* 803-9 and plasmid was prepared.

In this manner, the first half of the gene was amplified. This was cloned into pUC19 using the Pst I and Asp I sites incorporated in the ends of the primers. Sequencing revealed that it was the correct DNA that had been cloned, and the fragment was labelled using random hexamer primers with a-$^{32}$P-dATP whereupon a Southern hybridization was performed on *A. lyticus* chromosomal DNA cut with various restriction endonucleases. This indicated that the gene was situated on an approximately 2.1kb SphI-Nco I fragment.

A library was made from Sph I-Nco I digested *A. lyticus* DNA of approximately 2100 bp in size and cloned into Sph I-Nco I digested pSX54 (a pUC18 (Yanisch-Perron et al., supra) derived cloning vector). Around 10.000 colonies on 6 plates were lifted onto Whatman 540 ashless filters and hybridized at 65° C. with the probe described above (Sambrook el al. (1989), Molecular Cloning, Cold Harbor Laboratory Press). The filters were washed at the same temperature and placed onto X-ray films. After exposure it turned out that about 1% of the colonies were positive. 25 were reisolated and plasmids were prepared. These were cut with Pst I and EcoRI and 3 turned out to have the expected restriction pattern.

One of these (pSX494, FIG. 1) was digested with Nco I, filled out with Klenow polymerase and the four dNTP's, and digested with Sph I. The 2.1 kb band was isolated from an agarose gel and ligated into dephosphorylated Sph I-Sma I digested pUC19 giving rise to pSX512 (FIG. 2). The plasmid was transformed into E. coli W3110 lacl$^q$ (E. coli W3110 is an early isolate and has been used extensively as ancestral stock for the K-12 strain (B. Bachman, Bacteriol. Rev. 36, 1972). The W3110 strain used in the present method has been made lacl$^q$ in order to overproduce the Lac repressor, turning off expression from p/ac more completely). The resulting strain was shown to hydrolyse Z-lys (Benzoyl-lysyl-pNA) when induced with either IPTG or lactose. Western blot analysis (with antibodies raised against Achap I available from WAKO Co.) showed that the induced strain produced a protein that was too big compared to the known enzyme.

EXAMPLE 2

Figure 3:
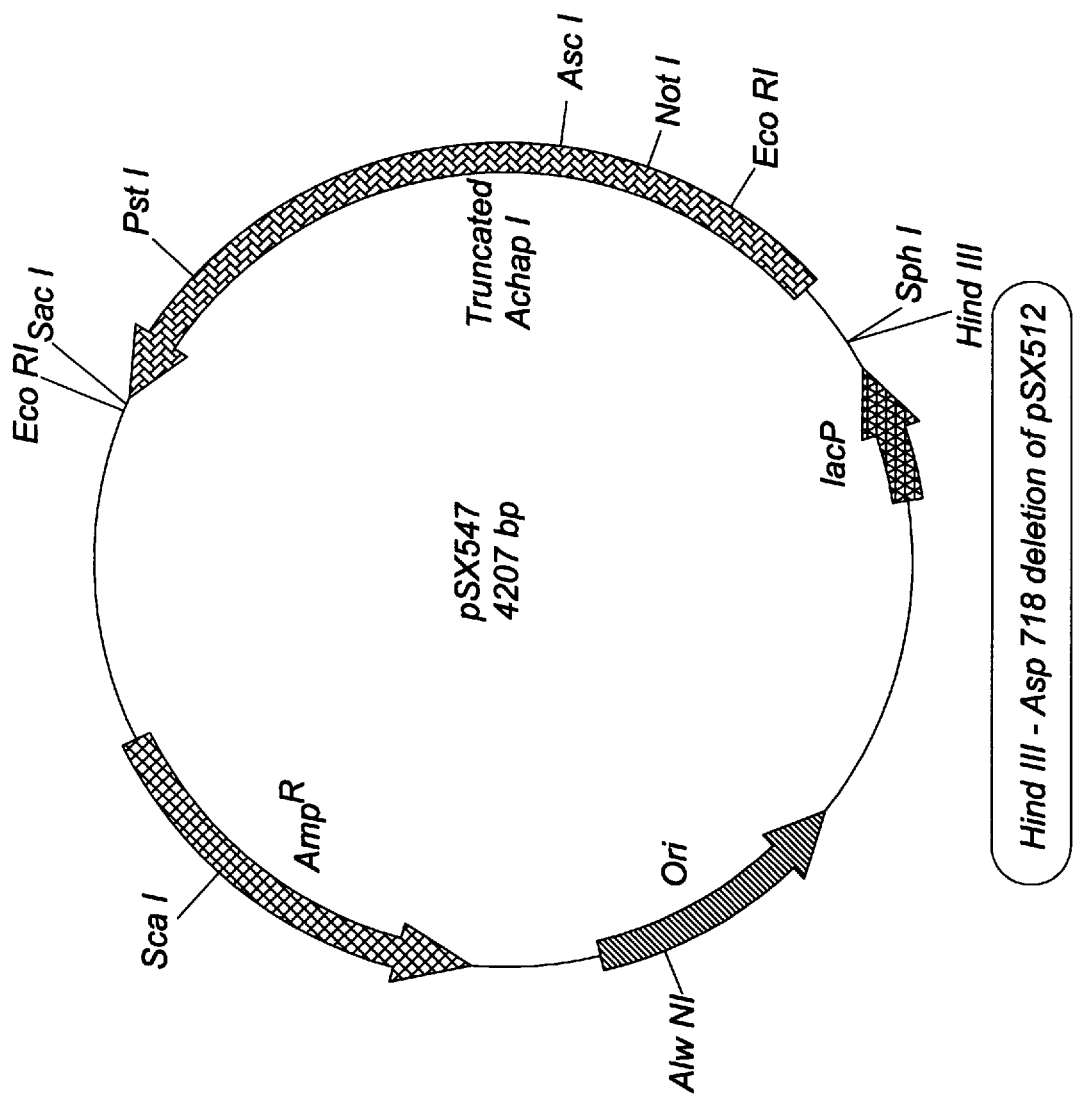

A new DNA construct was made wherein the 3'-end of the coding region was deleted meaning that the resulting protein would lack the C-terminal extension that is cleaved off in the original A. lyticus strain. Two UGA stop codons and a Hind III site was introduced by PCR in the A. lyticus gene at the site where the portion of the gene coding for the mature enzyme ends. This Hind III site was subsequently filled out with Klenow polymerase and ligated to the Asp 718 I site (also filled out) on pSX512 resulting in pSX547 (FIG. 3). This plasmid was transformed into E. coli W3110 lacl$^q$ and plated onto LB-plates with 200 μg/ml ampicillin (J. H. Miller (1972), Experiments in Molecular Genetics, Cold Spring Harbor Laboratory).

The resulting strain was grown in liquid LB medium containing 0.4% lactose for 44 hours at 26° C. whereafter the culture was centrifuged and the supernatant tested for lysyl-endopeptidase activity with Benzoyl-lysyl-pNA. The result was positive and a Western blot analysis (see above) showed that the enzyme produced from this strain had exactly the same size as the commercially available product (Achap I). It was also shown that the enzyme had the same specific activity.

EXAMPLE 3

A construct was made where the Humicola insolens lipase gene was fused to the Savinase (Subtilisin 309) signal sequence and the expression was under control by xylose:

pSX92 (WO 89/06279) was cut with Hind III, blunt ended with Klenow polymerase (-nucleotides), and then cut with Cla I. The large fragment was isolated (A).

pHLL (see EP 305,216 FIGS. 3 and 4) was cut with Bam HI, blunt ended like above, and then cut with Xho II. The fragment containing the mature part of the lipase gene was isolated (B, 818bp.)

Figure 4A:
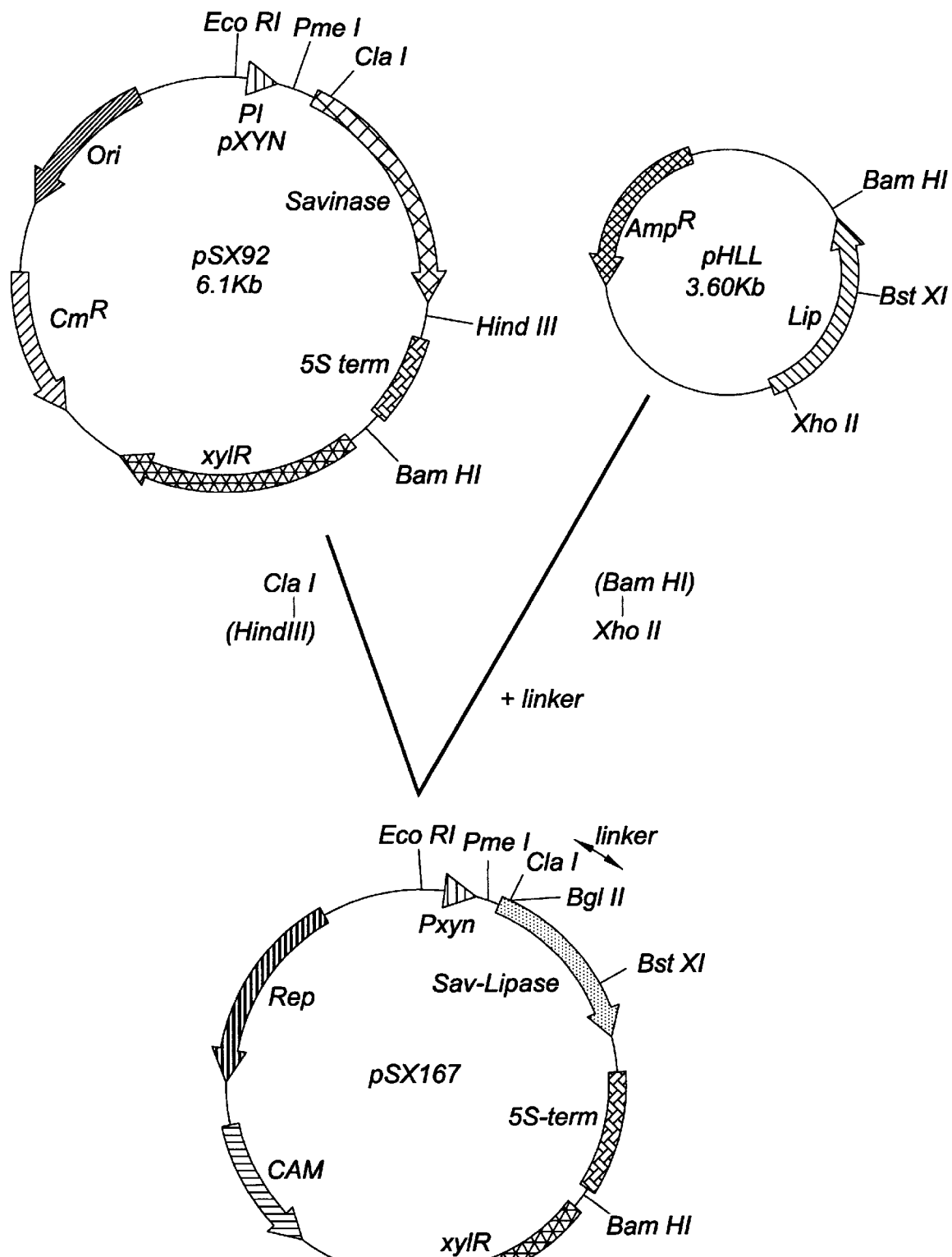

A and B were ligated together with a synthetic linker which codes for the last 5 amino acids in the Savinase signal fused to the first four amino acids of the mature lipase (FIG. 4a). The last A in the upper strand changes the Xho II site in the lipase gene to a Bgl II site:

```
KFN 575/576:  5'-CG ATC GCA TCG GCT GCT GAG GTC TCG CAA -3'

3'- TAG CGT AGC CGA CGA CTC CAG AGC GTT CTAG -5'

Savinase       |      lipase
```

Figure 4B:
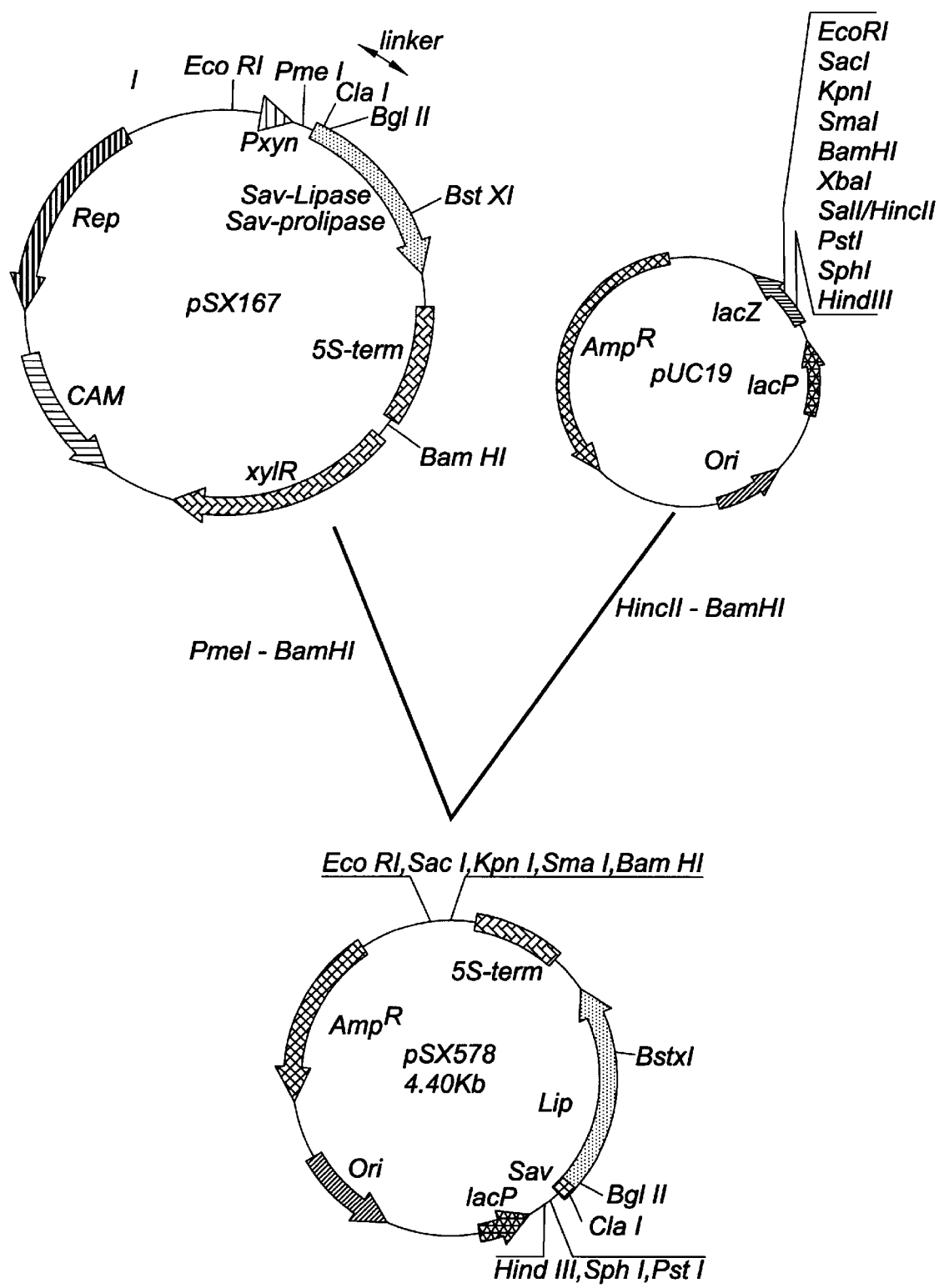

The resulting plasmid pSX167 was cut with Pme I and Bam HI and the fragment containing the Savinase-Lipase fusion and the 5S terminator was isolated (1769 bp.). This fragment was ligated into Hinc II-Bam HI cut pUC19 (Yanish-Perron et al. (1985) GENE 33, 103–119) giving rise to pSX578 (FIG. 4b).

The prepro-part of the A. lyticus protease gene was fused to the lipase using the PCR technique "splicing by overlap extension" described by Horton et al. (1989), GENE 77, 61–68.

Primers for the A. lyticus protease I prepre-mature H. insolens lipase fusion:

```
MHJ 3799:    5'- ACT CGGCGCGCCAAC TGT GGA CGG-3'
                         Asc I

MHJ 3952:

5'- GAC CTC TTTATCATCGTCGTCCTT CTC GCC GGA CGC AGC GGC CAG GC-3'
        lipase | Enterokinase site |     pro-A. lyticus protease MHJ 3829:    5'-GACGACGATGATAAAGAG GTC TCG CAA GAT CTG TTT AAC C-3'
                  Enterokinase site | mature lipase
```

-continued

```
MHJ 3800:   5'- CCA GAT TTG ATCCAGTACTCTGGG C-3'
                             Bst XI
```

Figure 4C:
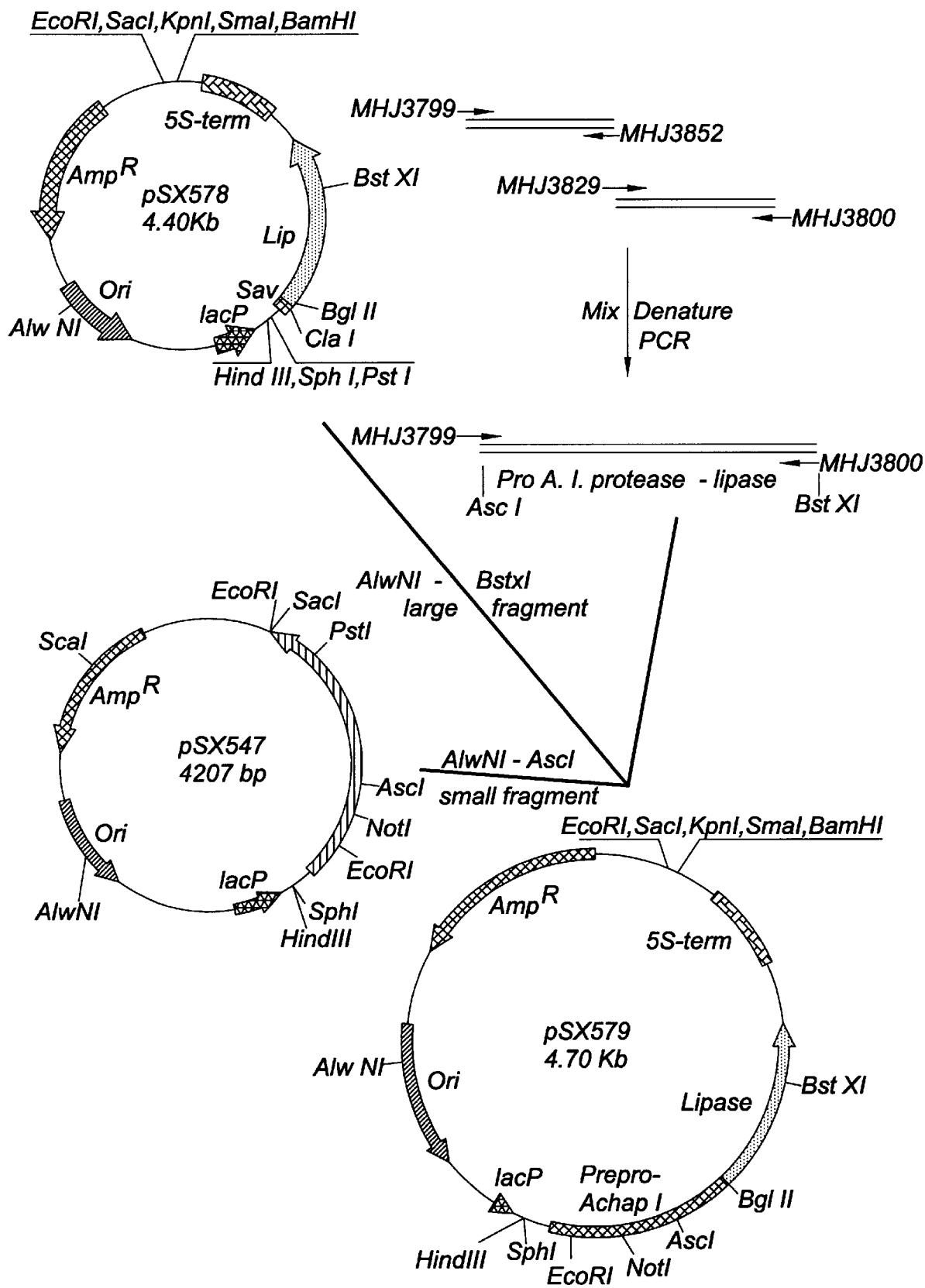

Two PCR products were made: MHJ 3799/MHJ 3852 with pSX547 as template and MHJ 3829/MHJ 3800 with pSX578 as template. These two products were mixed, denatured and a joined PCR product was made with MHJ 3799 and MHJ 3800 as primers. This was cut with Asc I and Bst XI and used in the construction of pSX579 (FIG. 4c). This plasmid was transformed into E. coli W3110 lacI$^q$ and the strain was cultivated as described in example 2.

EXAMPLE 4

The prepro-part of the B. subtilis Savinase gene (Subtilisin 309) was fused to the mature part of the lipase gene in the same way as above using the following primers:

```
MHJ 3790:   5'-AAA AAAGCTTGG AGA AAC CGA ATG AAG AAA C-3'
               Hin dIII          | Start Savinase MHJ 3851:
   5'-GAC CTC TTTATCATCGTCGTCCAT TGT CGT TAC TTC TGC ATC CTC-3'
      lipase | Enterokinase site |   Pro- Savinase
```

Figure 4D:
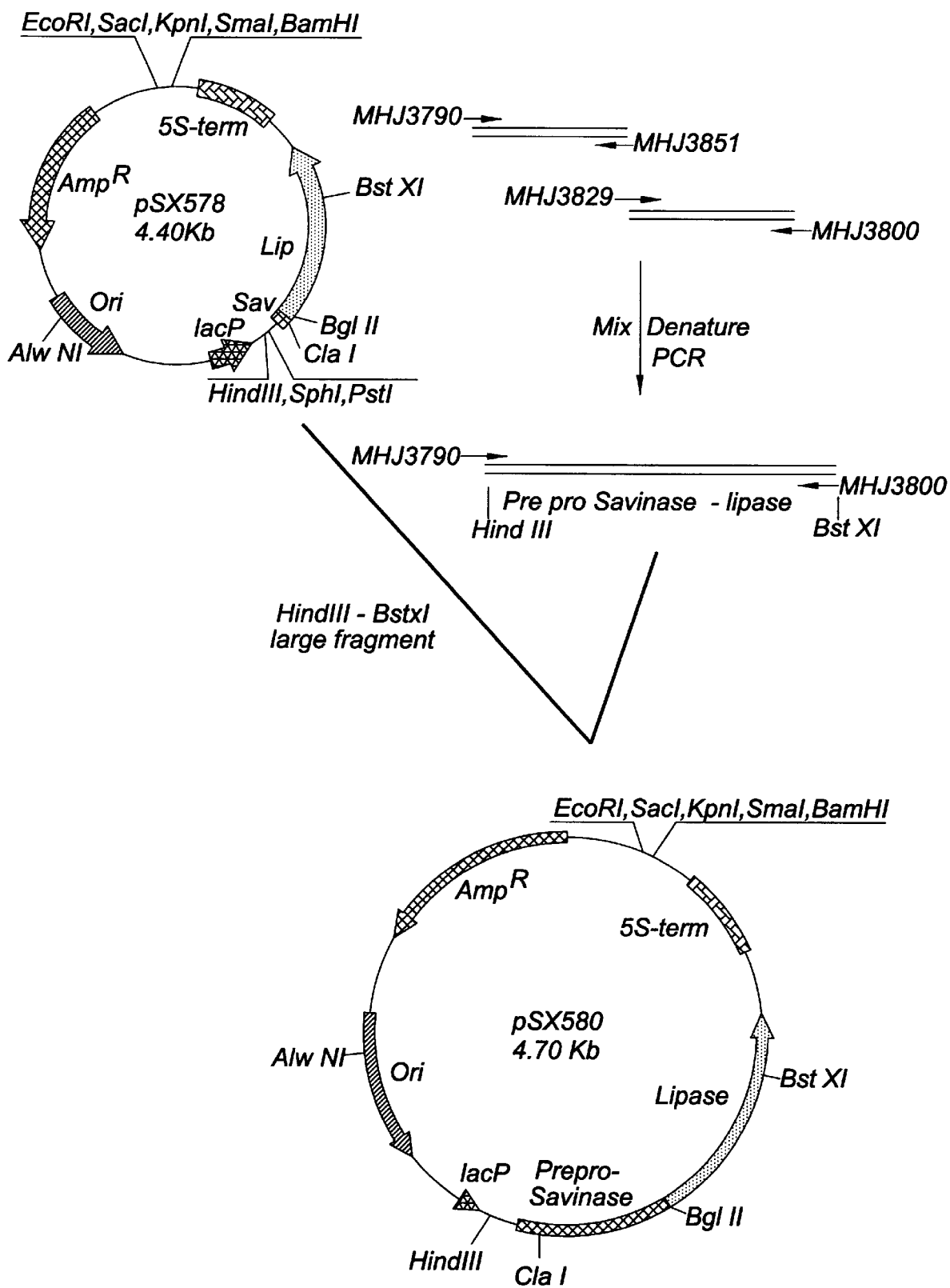

A PCR product was made using these primers and pSX92 as template (MHJ 3790 introduces a Hind III site right at the ribosome binding site in front of the Savinase initiation codon). This was mixed with the MHJ 3829/MHJ 3800 product from above, denatured and a joined product was made with MHJ 3790 and MHJ 3800 as primers. This was cut with Hind IIII and Bst Xl and used in the construction of pSX580 (FIG. 4d). This plasmid was transformed into E. coli W3110 lacI$^q$ and the strain was cultivated as described in example 2.

EXAMPLE 5

Expression in E. coli of glucagon-like peptide I fused to A. lyticus protease I prepro-region.

Figure 5:
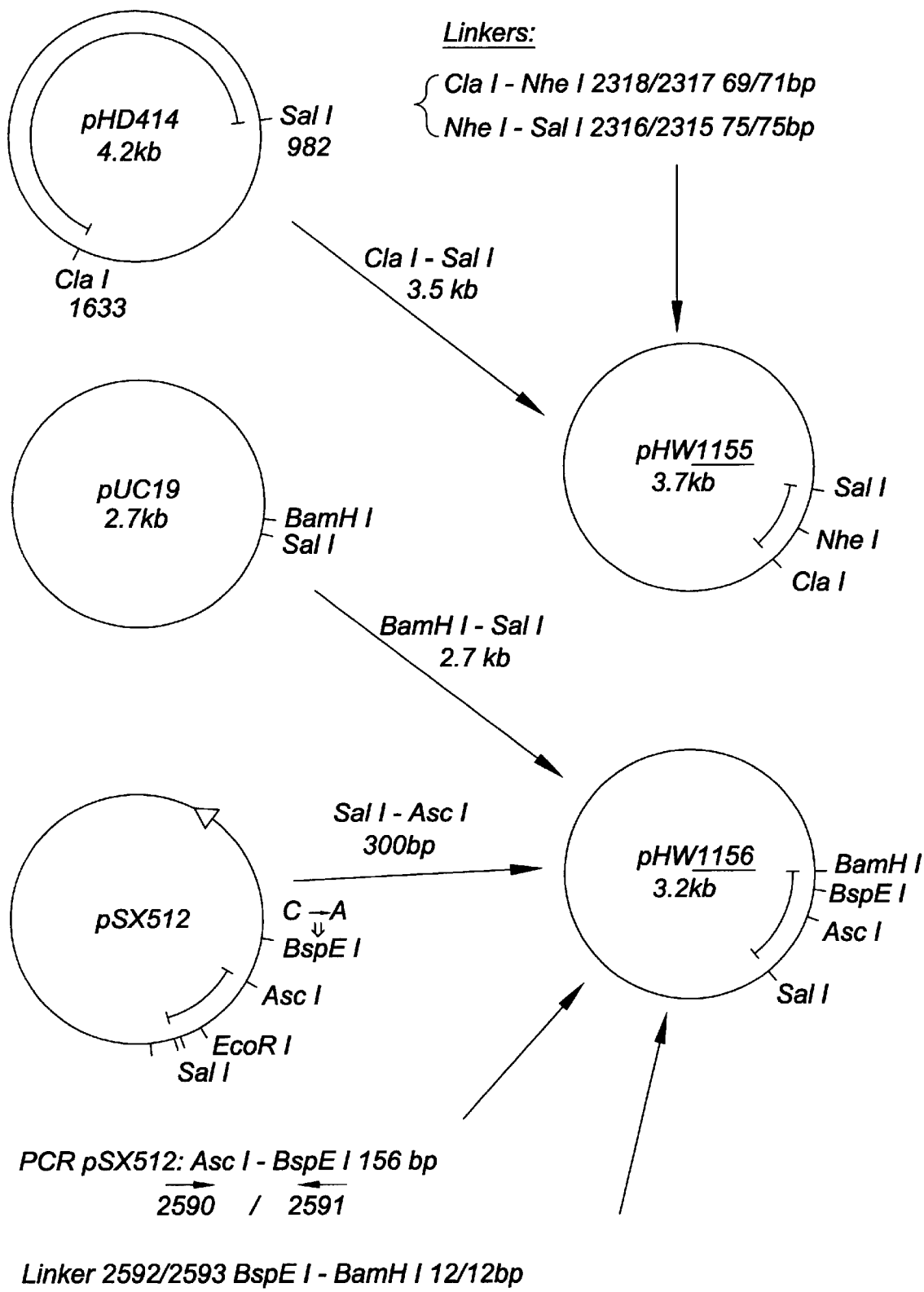
Figure 6:
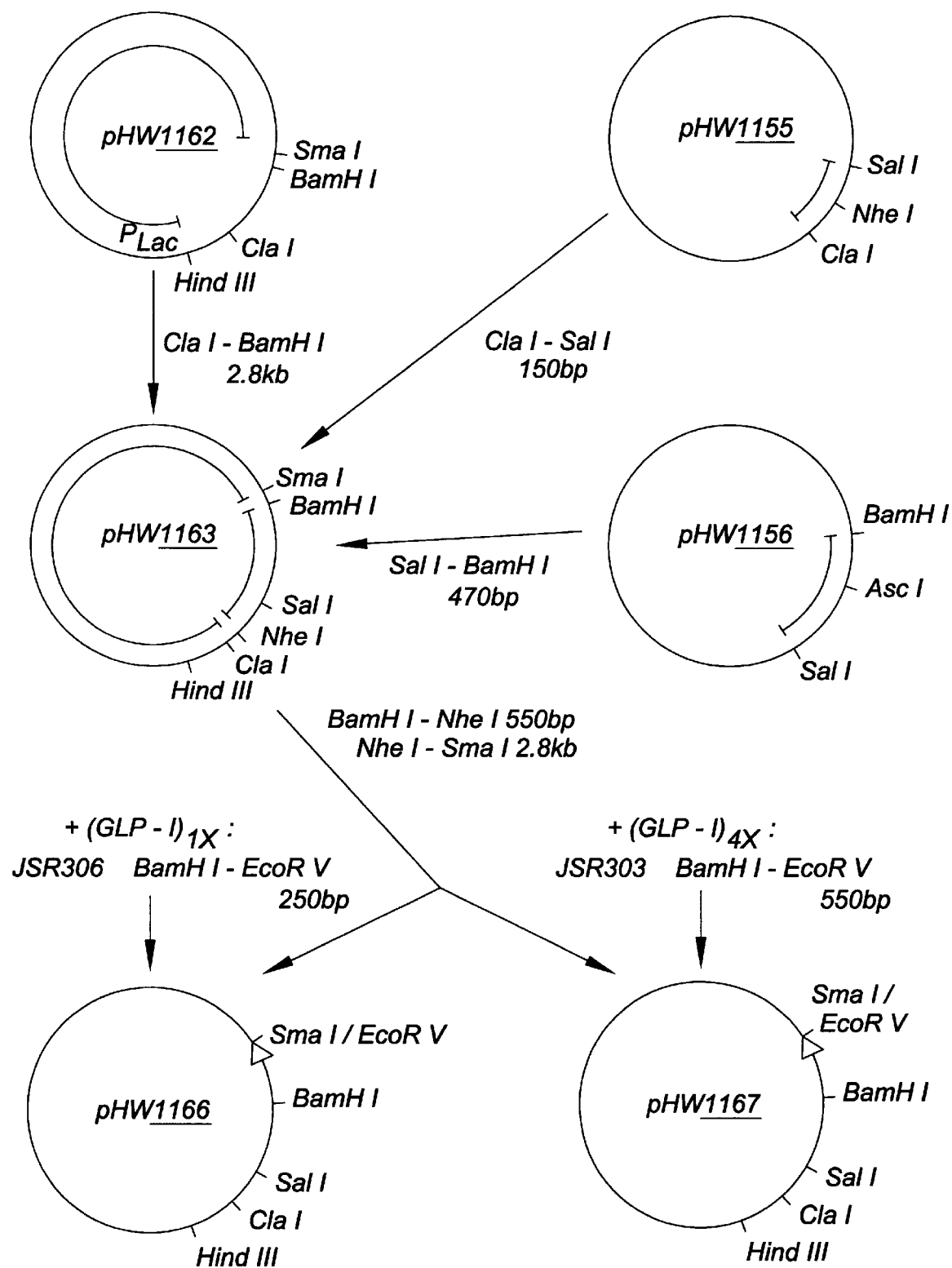

The construction of expression vectors for glucagon-like peptide I (GLP-1) fused to A. lyticus alkaline protease I (Achap I) prepro-region, is outlined in FIGS. 5–6. Oligonucleotide linkers coding for the protease signal peptide and the first 29 amino acids in the pro-region have the following sequence:

```
2318:  5'  CGATGAAACGTATCTGCGGATCCCTGCTGCTGCTGGGTCT

2317:  3'      TACTTTGCATAGACGCCTAGGGACGACGACGACCCAGA

GAGCATCAGCGCGGCGCTGGCGGCGCCGG       3'       2318

CTCGTAGTCGCGCCGCGACCGCCGCGGCCGATC   5'       2317

2316 :  5'  CTAGCCGTCCGGCGGCGTTCGATTATGCGAACCTGAGCAGCGTGGA

2315 :  3'      GGCAGGCCGCCGCAAGCTAATACGCTTGGACTCGTCGCACCT

TAAAGTGGCGCTGCGTACCATGCCGGCGG       3'       2316

ATTTCACCGCGACGCATGGTACGGCCGCCAGCT   5'       2315
```

The linker sequences, which are optimized for best codon usage in E.coli, were subcloned into the versatile vector pHD 414 (described in WO 92/16634), cut with Cla1 and Sal1. The C-terminal part of the pro-region from amino acid 30-185 was subcloned into pUC19 Sal1-BamH1 as described using pSX 512 (FIG. 2) for PCR priming with:

```
2590 : 5'  CAGCAACAACAACTCGGCGCGCC 3'

2591 : 3'  GCAGGCCTCTCTTCCCGCACAGC  5'
                              *
``` and the oligonucleotide linkers:

```
2592 : 5'  CCGGAGAACGTG      3'

2593 : 3'           TCTTGCACCTAG 5'
```

At position 185 the lysine residue has been substituted with arginine. A* is introduced in-stead of C in 2591 to create a BspE1 site.

The expression system shown in FIG. 6 is pUC19 containing the lac promoter. A Hind3-Cla1 linker, which is also adapted for the Tet promoter, was subcloned into pUC19 using a Cla1-BamH1 spacer fragment from pBR322. The linker sequences are as follows:

```
2737 : 5'  AGCTTTAATGCGGTAGTTTATCACAGTTAAATTG 3'

2747 : 3'       AATTACGCCATCAAATAGTGTCAA         5'
```

-continued

```
2748 : 5'      CTAACGCTTAAGGAGGTTAAT          3'
2738 : 3' TTTAACGATTGCGAATTCCTCCAATTAGC       5'
```

The promoter and linker were joined to the Achap I prepro-region in pHW1163, in which the GLP-1 gene was inserted as a BamH1-EcoRV fragment of 250 bp and 550 bp, respectively, corresponding to a monomer and a tetramer of the gene (prepared synthetically as described in DK 1440/93). The resulting expression plasmids pHW1166 and pHW1167 were transformed into *E. coli* W3110 lacI$^q$ and GLP-1 expression was measured in supernatants by Western blot analysis using specific antibodies. Processed as well as unprocessed material was detected in the supernatants.

EXAMPLE 6

Expression in *E. coli* of GLP-1 fused to *A. lyticus* protease pre-pro-core region inactivated by truncation.

Figure 7:
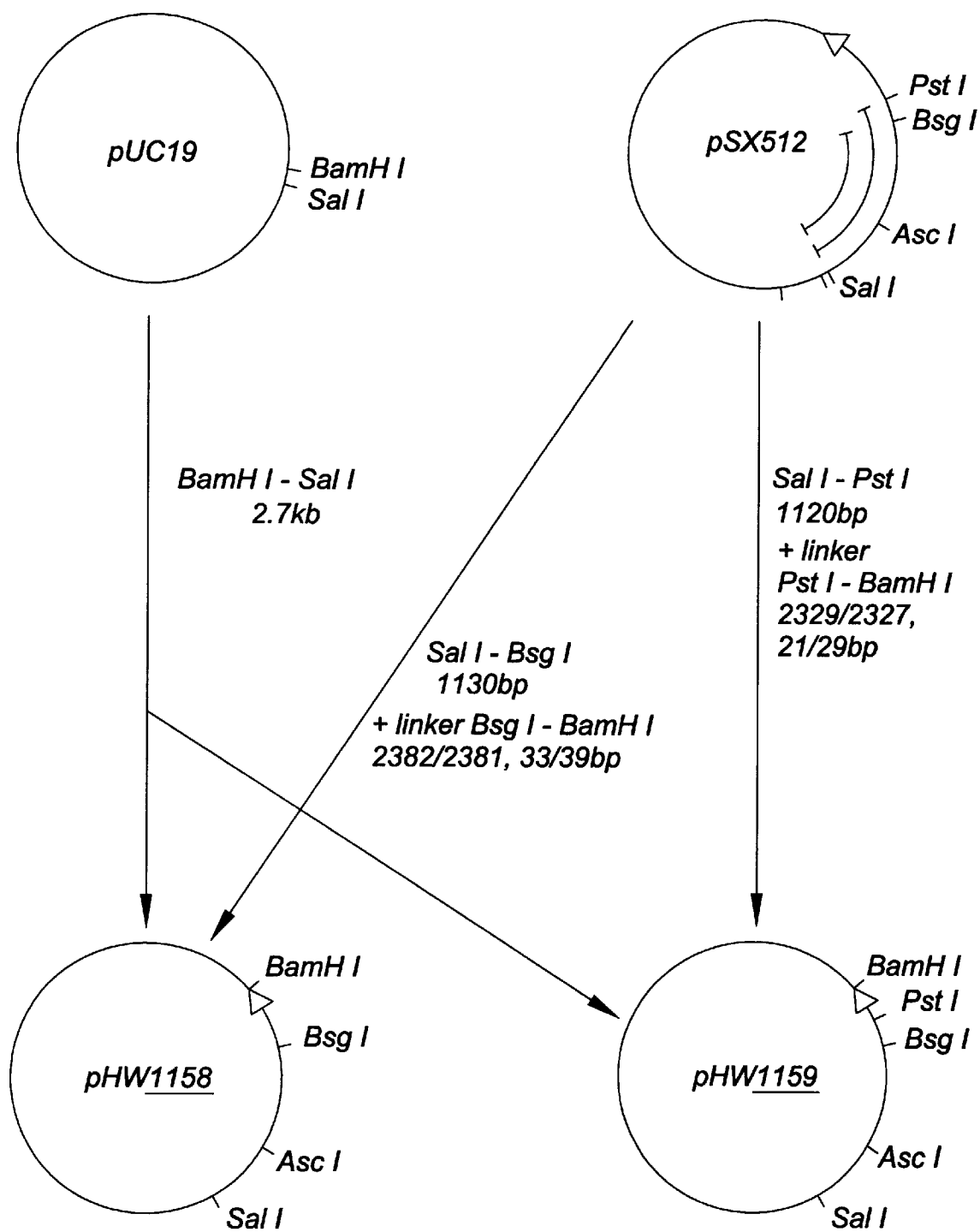

The core region codes for the mature enzyme, which can be inactivated by truncation. This has been done in two ways as shown in FIG. 7. Using a Bsg1-BamH1 linker

Figure 10:
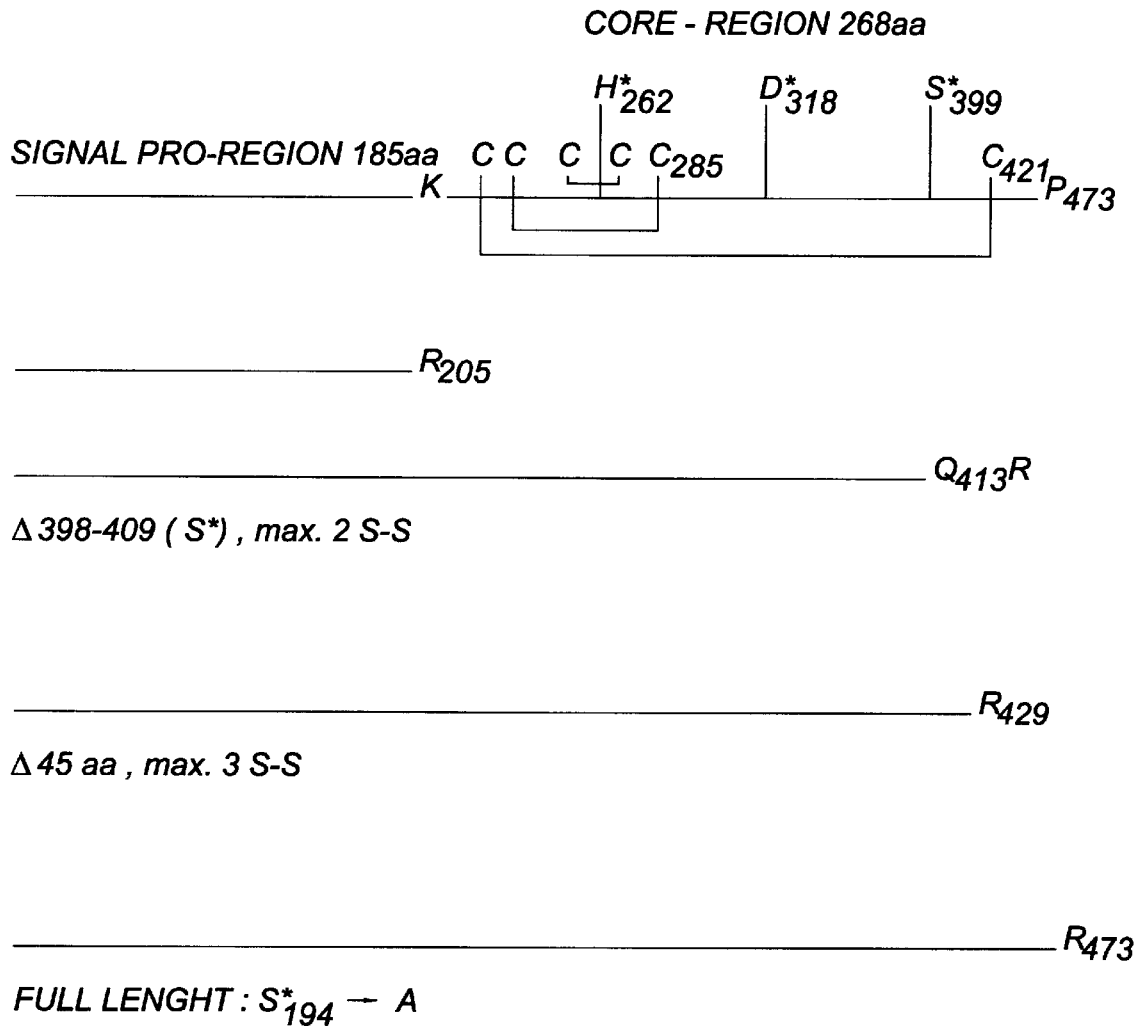

```
2382:5'    GTGTGACCGAACCGGGTGTGCTGGGTCAGCGTG       3'
2381:3' GCCACACTGGCTTGGCCCACACGACCCAGTCGCACCTAG    5'
``` the core region is deleted of 60 C-terminal amino acids and an additional deletion of 12 amino acids including serine in the catalytic triad as shown in FIG. 10.

Using a Pst1-BamH1 linker:

```
2329:5'         GCGCGACCGGCACCAACCGTG          3'
2327:3' ACGTCGCGCTGGCCGTGGTTGGCACCTAG          5'
``` the core region is deleted of 45 C-terminal amino acids, just leaving the possibility of creating all three sulphur bridges found in the native core.

Figure 8:
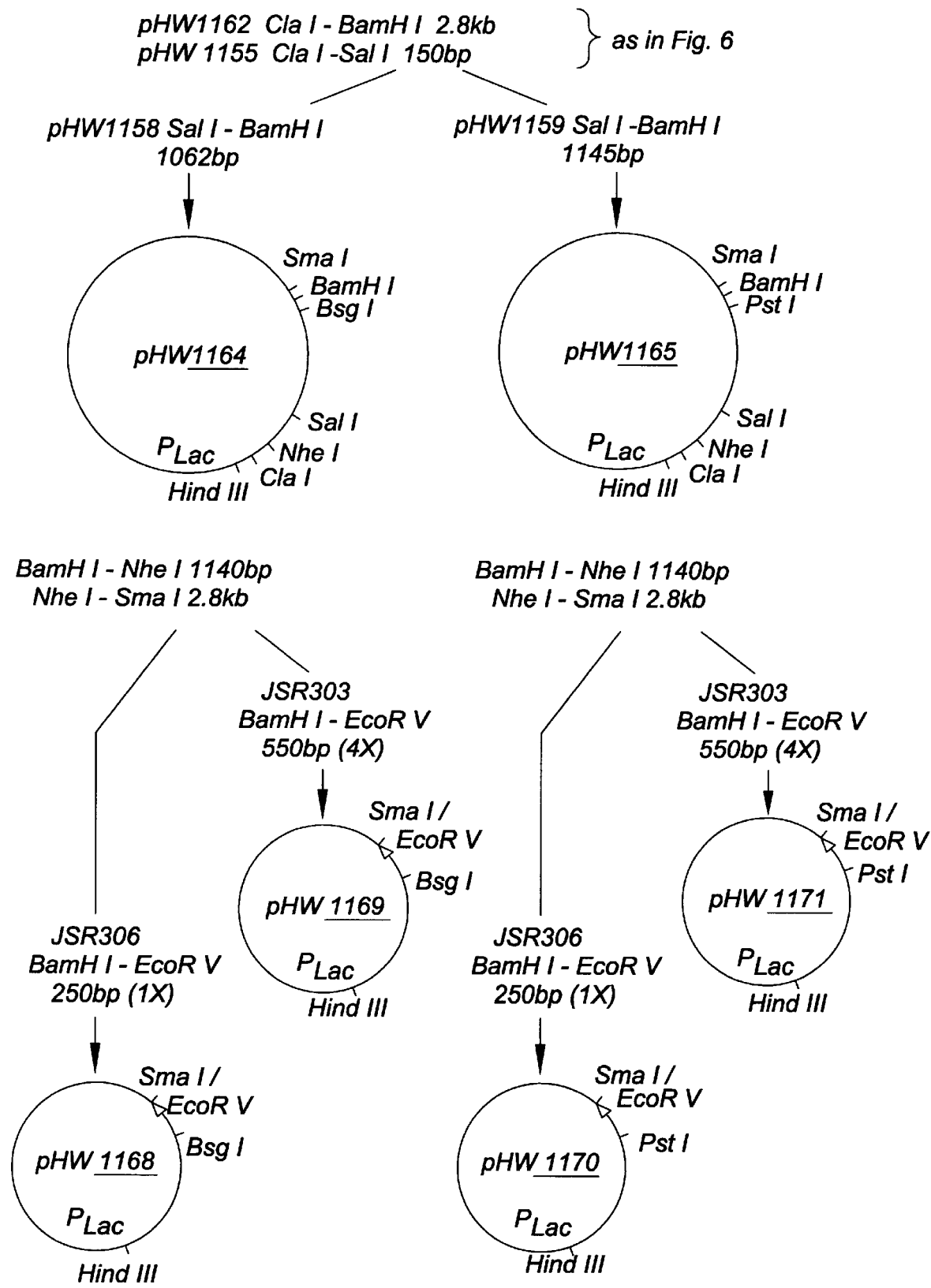

The linkers were joined to most of the Achap I gene starting from Sal1-site as described before to create pHW1158 and pHW1159. From there on the procedure to add promoter, N-terminal part of the Achap I gene and GLP-1 gene as monomer and as tetramer, is shown in FIG. 8. It follows the same pattern as described in FIG. 6 for the prepro-con-structions. The expression plasmids pHW1168-1171 were analyzed as described in Example 5. Processed and unprocessed material was detected in the culture supernatants.

EXAMPLE 7

Expression in *E. coli* of GLP-1 fused to *A. lyticus* protease prepro-core region inactivated by mutation.

Mutation without deletion is probably the best way to mimic the native situation as for folding of the core region and still prevent catalysis of the product. We have chosen to mutate the active serine residue to alanine by introducing a PCR fragment C-terminally, using pSX512 as template and the following primers:

```
3319:  5' CATTTGACCGTGCAGTGGCAGCCCTCGGGCGGCGT
          GACCGACCGGGTTCGGCGGGTTCG 3'

3320:  3' GTCAAGTAGCTACCGGACCTAAGCCCGCCGCCGTG
          CGGCGCGCCTAGGCGGCCACCGCTT 5'
```

Figure 9:
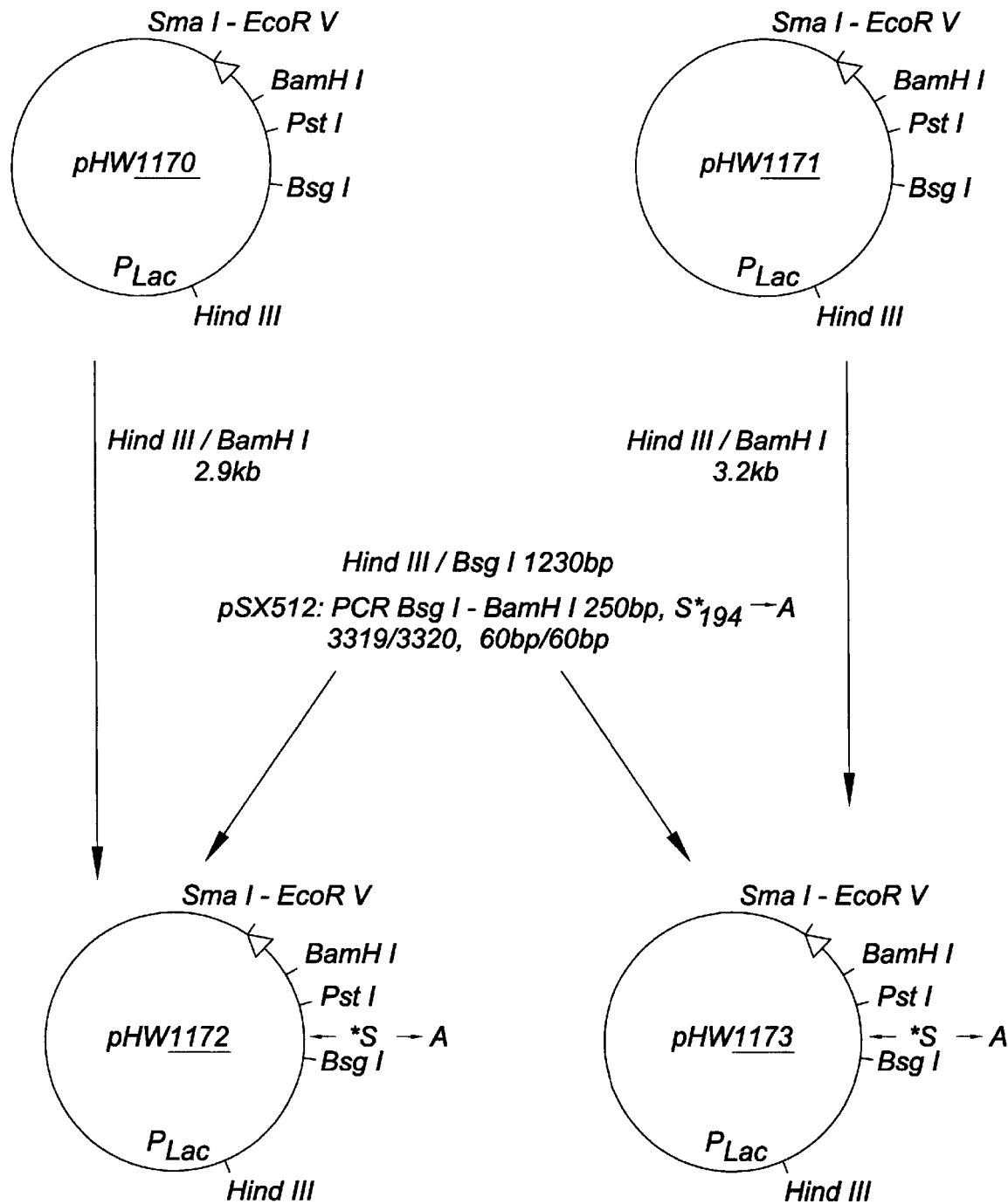

The procedure is depicted in FIG. 9. The resulting plasmids pHW1172 containing the GLP-1 monomer and pHW1173 containing the GLP-1 tetramer were analysed as described with the other constructions. Processed and unprocessed material was detected in the culture supernatants.

All the constructions of examples 5–7 are summarized in FIG. 10.

What is claimed is:

1. A method for producing an extracellular protein in a bacterium, the method comprising
   a) providing a recombinant vector including a DNA construct encoding a fusion protein, wherein said fusion protein comprises an N-terminal prepropeptide, but not a C-terminal propeptide, of *Achromobacter lyticus* protease I, corresponding to residues 1–205 of SEQ ID NO:27, fused to a polypeptide sequence comprising a desired protein;
   (b) transforming cells of a bacterium having an inner and outer cell membrane with the recombinant vector of step (a);
   (c) culturing the transformed cells of step (b) under conditions permitting expression of the fusion protein and
   (d) recovering the fusion protein, the desired protein, or both from the extracellular medium.

2. The method of claim 1, wherein the fusion protein is transported out of the cell by secretion across both the inner and outer cell membrane.

3. The method of claim 1, wherein the fusion protein is transported out of the cell by export of the protein to the periplasm followed by lysis of the outer membrane.

4. The method of claim 1, wherein the fusion protein is transported out of the cell by export of the protein to the periplasm followed by release from the outer cell membrane.

5. The method of claim 4, wherein the fusion protein further comprises a peptide sequence of *Achromobacter lyticus* protease I SEQ ID NO:27 sufficient to facilitate transport of the desired protein out of said transformed cells.

6. The method of claim 5, wherein the fusion protein comprises full-length *Achromobacter lyticus* protease I core protein.

7. The method of claim 6, wherein the *Achromobacter lyticus* protease I is in an active form.

8. The method of claim 6, wherein the *Achromobacter lyticus* protease I is in an inactive form.

9. The method of claim 1, wherein the desired protein is selected from the group consisting of *Achromobacter lyticus* protease I core protein, glucagon-like peptide-1, growth hormone, tissue factor pathway inhibitor, aprotinin, trypsin, insulin, and an insulin precursor or analogue.

10. The method of claim 1, wherein the bacterium is a gram-negative bacterium.

11. The method of claim 10, wherein the gram-negative bacterium is *Escherichia coli*.

12. The method of claim 1, wherein the fusion protein is subjected to a maturation procedure.

13. A recombinant expression vector including a DNA construct comprising a DNA sequence encoding an N-terminal prepropeptide, but not a C-terminal propeptide, of *Achromobacter lyticus* protease I preceding and fused in frame to a DNA sequence encoding a desired protein.

14. The vector of claim 1, wherein the DNA construct further comprises a DNA sequence encoding at least part of the *Achromobacter lyticus* protease I.

15. The vector of claim 14, wherein the DNA construct comprises a DNA sequence encoding the full-length *Achromobacter lyticus* protease I core protein.

16. The vector of claim 13, wherein the desired protein is selected from the group consisting of *Achromobacter lyticus* protease I core protein, glucagon-like peptide-1, growth hormone, tissue factor pathway inhibitor, aprotinin, trypsin, insulin, and an insulin precursor or analogue.

17. A DNA construct comprising a DNA sequence encoding an N-terminal prepropeptide, but not a C-terminal propeptide, of *Achromobacter lyticus* protease I preceding and fused in frame to a DNA sequence encoding a desired protein.

18. The DNA construct of claim 17, wherein the DNA construct further comprises a DNA sequence encoding a peptide of the *Achromobacter lyticus* protease I SEQ ID NO:27 sufficient to facilitate extracellular transport of the desired protein fused in frame to the sequence encoding the desired protein.

19. The DNA construct of claim 18, which comprises a DNA sequence encoding the full-length *Achromobacter lyticus* protease I core protein.

20. The DNA construct of claim 17, wherein the desired protein is selected from the group consisting of *Achromobacter lyticus* protease I core protein, glucagon-like peptide-1, growth hormone, tissue factor pathway inhibitor, aprotinin, trypsin, insulin, and an insulin precursor or analogue.

21. A method for producing an extracellular protein in a bacterium, the method comprising
   (a) transforming cells of a bacterium having an inner and outer cell membrane with a recombinant vector including a DNA construct comprising a DNA sequence encoding a fusion protein, wherein said fusion protein comprises an N-terminal prepropeptide, but not a C-terminal propeptide, of *Achromobacter lyticus* protease I, corresponding to residues 1–205 of SEQ ID NO:27, fused to a polypeptide sequence comprising a desired protein;
   (b) culturing the transformed cells of step (a) under conditions permitting expression of the fusion protein; and
   (c) recovering the fusion protein, the desired protein, or both from the medium.

22. A method for producing an extracellular protein in a bacterium, the method comprising
   (a) transforming cells of a bacterium having an inner and outer cell membrane with a recombinant vector including a DNA construct comprising a DNA sequence encoding a fusion protein, wherein said fusion protein comprises an N-terminal prepropeptide, but not a C-terminal propeptide, of *Achromobacter lyticus* protease I, corresponding to residues 1–205 of SEQ ID NO:27, fused to a desired protein;

(b) culturing the transformed cells of step (a) under conditions permitting expression of the fusion protein and leakage of the fusion protein through transport out of the cell either by secretion across both the inner and outer cell membrane, or by export of the protein to the periplasm followed by partial lysis of the outer membrane, or release from the outer membrane into the culture medium; and (c) recovering the resulting fusion protein, desired protein, or both from the medium.

* * * * *

UNITED STATES PATENT AND TRADEMARK OFFICE
CERTIFICATE OF CORRECTION

| | |
|---|---|
| PATENT NO. | : 6,171,823 B1 |
| DATED | : January 9, 2001 |
| INVENTOR(S) | : Wöldike et al. |

Figure 2:
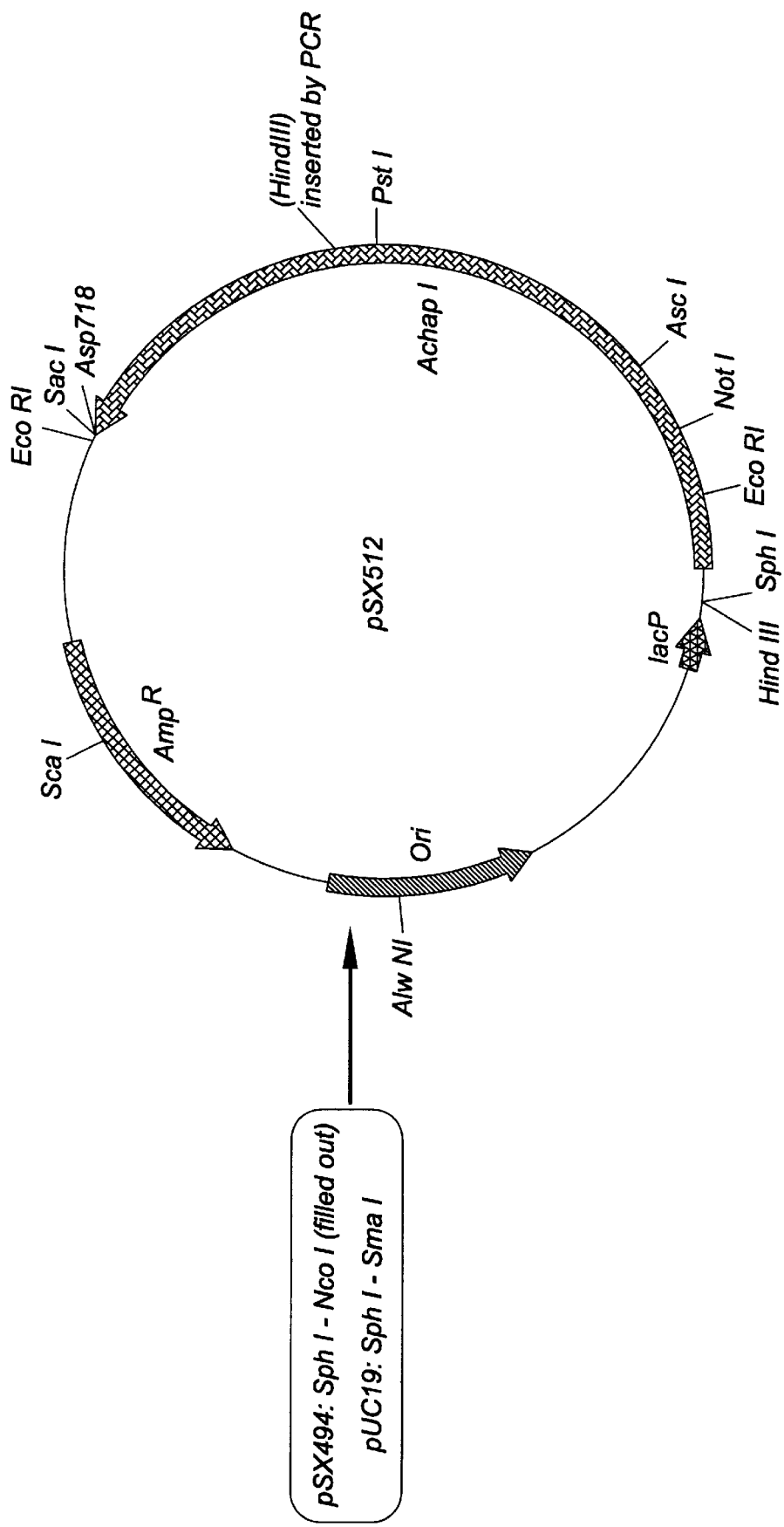

It is certified that error appears in the above-identified patent and that said Letters Patent is hereby corrected as shown below:

Column 3,
Line 31, please insert:
-- BRIEF DESCRIPTION OF THE DRAWINGS
   Figure 1 is a schematic representation of the construction of plasmid pSX494.
   Figure 2 is a schematic representation of pasmid pSX512.
   Figure 3 is a schematic representation of plasmid pSX547.
   Figure 4a is a schematic representation of the construction of plasmid pSX167.
   Figure 4b is a schematic representation of the construction of plasmid pSX578.
   Figure 4c is a schematic representation of the construction of plasmid pSX579.
   Figure 4d is a schematic representation of the construction of plasmid pSX580.
   Figure 5 is a schematic representation of the consturction of plasmids pHW1155 and pHW1156.
   Figure 6 is a schematic representation of the construction of plasmids pHW1166 and pHW1167.
   Figure 7 is a schematic representation of the construction of plasmids pHW1158 and pHW1159.
   Figure 8 is a schematic representation of the construction of plasmids pHW1168 and pHW1169, pHW1170, and pHW1171.
   Figure 9 is a schematic representation of the construction of plasmids pHW1172 and pHW1173.
   Figure 10 is a schematic representation of fusion proteins between glucagons-like peptide 1 (GLP-1) and *A. lyticus* protease I preproregion.
   Figure 11 is a schematic representaton of the domain structure of *A. lyticus* protease I. --

Signed and Sealed this

Thirteenth Day of November, 2001

*Attest:*

NICHOLAS P. GODICI
*Acting Director of the United States Patent and Trademark Office*

*Attesting Officer*